United States Patent
Seo et al.

(10) Patent No.: US 8,530,585 B2
(45) Date of Patent: Sep. 10, 2013

(54) CROSSLINKER, CROSSLINKED POLYMER MATERIAL, AND PRODUCTION METHOD OF THE CROSSLINKED POLYMER MATERIAL

(75) Inventors: Akishige Seo, Kiyosu (JP); Hideyuki Imai, Kiyosu (JP); Naoki Iwase, Kiyosu (JP); Toshikazu Takata, Tokyo (JP); Yasuhito Koyama, Tokyo (JP); Morio Yonekawa, Tokyo (JP)

(73) Assignees: Toyoda Gosei Co., Ltd., Aichi-pref. (JP); Tokyo Institute of Technology, Tokyo (JP)

( * ) Notice: Subject to any disclaimer, the term of this patent is extended or adjusted under 35 U.S.C. 154(b) by 286 days.

(21) Appl. No.: 13/030,583

(22) Filed: Feb. 18, 2011

(65) Prior Publication Data
US 2011/0224380 A1    Sep. 15, 2011

(30) Foreign Application Priority Data

Mar. 9, 2010  (JP) .................................. 2010-051664
Aug. 18, 2010  (JP) .................................. 2010-182864

(51) Int. Cl.
*C08F 8/30* (2006.01)
*C08F 120/44* (2006.01)

(52) U.S. Cl.
USPC .................. 525/329.1; 525/328.3; 525/331.7; 525/332.5; 558/299

(58) Field of Classification Search
USPC ...... 525/329.1, 328.3, 331.7, 332.5; 558/299
See application file for complete search history.

(56) References Cited

U.S. PATENT DOCUMENTS 6,355,826 B1 * 3/2002 Parker ........................... 558/299
2006/0173137 A1  8/2006 McGlothlin et al.
2007/0251572 A1 11/2007 Hoya et al.

FOREIGN PATENT DOCUMENTS

JP        A-11-180943         7/1999

OTHER PUBLICATIONS

Final Office Action issued by the U.S. Patent Office on Jul. 19, 2012 in connection with U.S. Appl. No. 12/659,128.
Office Action issued by the U.S. Patent Office on Nov. 28, 2011 in connection with U.S. Appl. No. 12/659,128.
Office Action issued by the U.S. Patent Office on Oct. 17, 2012 in connection with U.S. Appl. No. 12/659,128.
U.S. Appl. No. 12/659,128, filed Feb. 25, 2010, Seo et al.
Office Action mailed Mar. 12, 2013 in corresponding JP Application No. 2009-200716.

* cited by examiner

*Primary Examiner* — Ling Choi
*Assistant Examiner* — Chun-Chen Wang
(74) *Attorney, Agent, or Firm* — Posz Law Group, PLC

(57) ABSTRACT

The present invention provides a crosslinker used for crosslinking a polymer material having, in the molecule thereof, a multiple bond reactable with a nitrile oxide, the crosslinker including a bifunctional nitrile oxide having an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, wherein two such aromatic nitrile oxide derivative structures are bonded to either two oxy groups of a di-oxy structure having the two oxy groups or two carbonyl groups of a di-carbonyl structure having the two carbonyl groups.

14 Claims, 5 Drawing Sheets

F I G. 1
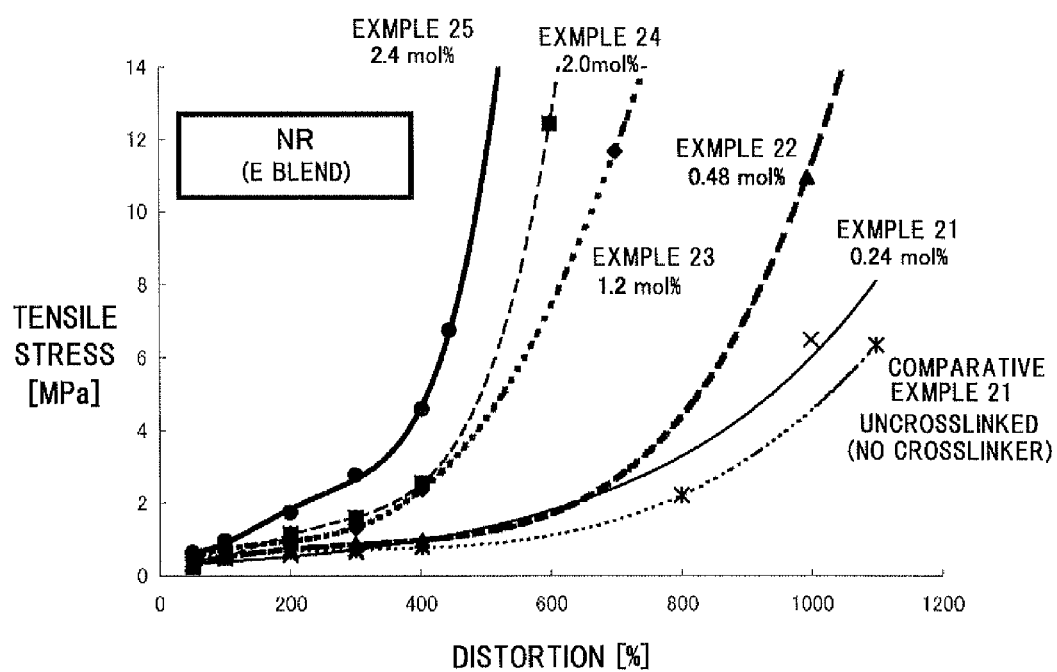

CROSSLINKER, CROSSLINKED POLYMER MATERIAL, AND PRODUCTION METHOD OF THE CROSSLINKED POLYMER MATERIAL

TECHNICAL FIELD

The present invention relates to a crosslinker, a crosslinked polymer material produced by crosslinking a polymer material, and a production method of the crosslinked polymer material.

BACKGROUND ART

The crosslinking of a rubber having in the molecule thereof a carbon-carbon double bond such as EPDM, NR, and NBR is generally performed using sulfur. A practical vulcanizing temperature for crosslinking these rubbers using sulfur is necessary to be 150° C. to 200° C. Therefore, these crosslinked rubbers have such a concern that rubber properties thereof are lowered by a thermal degradation during crosslinking as the vulcanizing temperature becomes higher. Moreover, for heating a rubber or the like, much energy is required. Therefore, it is studied to lower the vulcanizing temperature, and as one method therefor, a method of using a combination of various accelerators or the like is studied. However, by this method, the vulcanizing time becomes undesirably longer, so that such a study does not become commercially practical.

On the other hand, as a crosslinker for crosslinking a rubber at a low temperature, Patent Document 1 describes a polynitrile oxide having, in the molecule thereof, a plurality of nitrile oxide groups such as mesitylene dinitrile oxide (MDNO).

CITATION LIST

Patent Literature

Patent Literature 1: Japanese Patent Application Publication No. JP-A-11-180943

SUMMARY OF INVENTION

Technical Problem

However, a compound having two nitrile oxide groups in one aromatic ring such as mesitylene dinitrile oxide and a compound having a hydrogen atom at an ortho-position of a nitrile oxide group, that is, a compound in which a substituent is not introduced at an ortho-position of a nitrile oxide group, have poor stability (see paragraphs 0056 and 0057), so that such compounds can not be used as a crosslinker.

Thus, in view of the above, the present invention provides a crosslinker capable of crosslinking a polymer material having, in the molecule thereof, a carbon-carbon double bond, a nitrile group, or the like, such as NBR, at a vulcanizing temperature lower than that of a conventional crosslinker, a crosslinked polymer material produced by crosslinking a polymer material such as NBR with this crosslinker, and a production method of the crosslinked polymer material.

Solution to Problem

In view of the above, a crosslinker according to an aspect of the present invention is a crosslinker used for crosslinking a polymer material having, in the molecule thereof, a multiple bond reactable with a nitrile oxide, containing a bifunctional nitrile oxide having an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, in which two such aromatic nitrile oxide derivative structures are bonded to either two oxy groups of a di-oxy structure having the two oxy groups or two carbonyl groups of a di-carbonyl structure having the two carbonyl groups.

In view of the above, a production method of a crosslinked polymer material according to an aspect of the present invention is a method including crosslinking a polymer material using a bifunctional nitrile oxide having an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, in which two such aromatic nitrile oxide derivative structures are bonded to either two oxy groups of a di-oxy structure having the two oxy groups or two carbonyl groups of a di-carbonyl structure having the two carbonyl groups to produce the crosslinked polymer material.

In view of the above, a crosslinked polymer material according to an aspect of the present invention is produced by crosslinking a polymer material with a bifunctional nitrile oxide having an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, in which two such aromatic nitrile oxide derivative structures are bonded to either two oxy groups of a di-oxy structure having the two oxy groups or two carbonyl groups of a di-carbonyl structure having the two carbonyl groups.

The aspect of each element of the present invention is exemplified below.

1. Bifunctional Nitrile Oxide

The bifunctional nitrile oxide is not particularly limited. However, the bifunctional nitrile oxide has an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, and two such aromatic nitrile oxide derivative structures are bonded to either two oxy groups of a di-oxy structure having two oxy groups or two carbonyl groups of a di-carbonyl structure having two carbonyl groups. Thus, the stability of the bifunctional nitrile oxide is enhanced, and the bifunctional nitrile oxide can be used as a crosslinker.

Although the aromatic ring is not particularly limited, the aromatic ring is preferably an aromatic ring other than a heterocycle such as a benzene ring and a naphthalene ring.

Although the substituent is not particularly limited, examples thereof include a hydrocarbon group such as an alkyl group and an aryl group, and an oxy group. In terms of more enhancing the stability, the substituent is preferably an oxy group.

Here, although the alkyl group is not particularly limited, examples thereof include straight-chain or branched $C_{1-20}$ alkyl groups, and preferred examples thereof include straight-chain or branched $C_{1-4}$ alkyl groups such as a methyl group, an ethyl group, an n-propyl group, an isopropyl group, an n-butyl group, a sec-butyl group, an isobutyl group, and a tert-butyl group.

Although the oxy group is not particularly limited, examples thereof include hydrocarbon oxy groups such as an alkoxy group. Then, in the case of a benzonitrile oxide derivative structure in which the aromatic ring is a benzene ring, at least one of the oxy groups is preferably an alkoxy group. In two substituents of the benzonitrile oxide derivative structure, when one substituent is an alkoxy group, the other substituent is preferably an oxy group of the above-described di-oxy structure.

Here, although the alkoxy group is not particularly limited, examples thereof include straight-chain or branched $C_{1-4}$ alkoxy groups, and preferred examples thereof include straight-chain or branched $C_{1-3}$ alkoxy groups such as a methoxy group, an ethoxy group, an n-propoxy group, and an isopropoxy group.

Specific examples of the bifunctional nitrile oxide include the following four compounds.
3,3'-[1,3-phenylenebis(carbonyl)]bis(2,6-dimethoxybenzonitrile oxide)
2,2'-[methylenebis[(2,6-dimethyl-4,1-phenylene)oxy]]bis(6-methoxybenzonitrile oxide)
2,2'-[isopropylidenebis[(2,6-dimethyl-4,1-phenylene)oxy]]bis(6-methoxybenzonitrile oxide)
2,2'-octamethylenebis(oxy)bis(1-naphthonitrile oxide)

2. Polymer Material

The polymer material is not particularly limited so long as it is a polymer material having, in the molecule thereof, a multiple bond reactable with a nitrile oxide for being crosslinked by a bifunctional nitrile oxide.

Here, although the multiple bond reactable with a nitrile oxide is not particularly limited, examples thereof include C=S, N=N, P(V)=C, C=P(III), C=As, C=C, C=N, C=Se, B=N, C=P, C≡C, P(V)=N, C≡N, and C=O.

Specific examples of the polymer material include PAN (polyacrylonitrile) having in the molecule thereof a nitrile group (C≡N), NR (natural rubber) having in the molecule thereof a carbon-carbon double bond (C=C), EPDM (ethylene-propylene-diene copolymer rubber), and NBR (nitrile rubber) having in the molecule thereof a nitrile group and a carbon-carbon double bond.

3. Crosslinking Process

The crosslinking process for crosslinking the polymer material with a bifunctional nitrile oxide is preferably performed without using an organic solvent, because, by doing so, it is not necessary to provide an exhaust system, a recovery system of an organic solvent, or the like. The crosslinking process is more preferably performed within a kneading apparatus, because a conventional system used during crosslinking using sulfur can be utilized.

Here, although the kneading apparatus is not particularly limited, examples thereof include a closed kneading machine such as a Banbury mixer and Intermix, and an extruder such as a twin-screw extruder, a single-screw extruder, and a multi-screw extruder.

On the other hand, the crosslinking process is preferably performed in an organic solvent, because, by doing so, a molded article in a thin sheet shape or the like can easily be produced.

Here, although the organic solvent is not particularly limited, it is preferably a solvent capable of easily dissolving both the polymer material and the bifunctional nitrile oxide. Specific examples thereof include chloroform, DMF (N,N-dimethylformamide), and acetone.

The temperature for the crosslinking process is not particularly limited so long as the temperature is a temperature at which a polymer material can be crosslinked by a bifunctional nitrile oxide, that is, a polymer material and a bifunctional nitrile oxide can be reacted with each other. However, a crosslinking reaction is a chemical reaction, so that when the temperature is high, the reaction is accelerated, and when a temperature control such as heating is not performed, the management of the production process becomes easy. In this regard, the temperature for the crosslinking process is preferably 0° C. to 200° C. Further, when the polymer material is a material having at least a carbon-carbon double bond as a multiple bond such as NBR, NR, and EPDM, the temperature is more preferably 20° C. to 200° C., and when the polymer material is a material having only a nitrile group as a multiple bond such as PAN, the temperature is more preferably 50° C. to 200° C.

Advantageous Effects of Invention

According to some aspects of the present invention, there can be provided: a crosslinker capable of crosslinking a polymer material having, in the molecule thereof, a carbon-carbon double bond, a nitrile group, or the like, such as NBR, either at a vulcanizing temperature (for example, 20° C. to 150° C.) lower than an ordinary vulcanizing temperature, or at an ordinary vulcanizing temperature (for example, 150° C. to 200° C.) in a shorter time; a crosslinked polymer material produced by crosslinking a polymer material such as NBR with the crosslinker; and a production method of the crosslinked polymer material.

BRIEF DESCRIPTION OF DRAWINGS

FIG. 1 is a graph showing a relationship between distortion and tensile stress in NR in which a bifunctional nitrile oxide E is blended;

DESCRIPTION OF EMBODIMENTS

Examples

Figure 2:
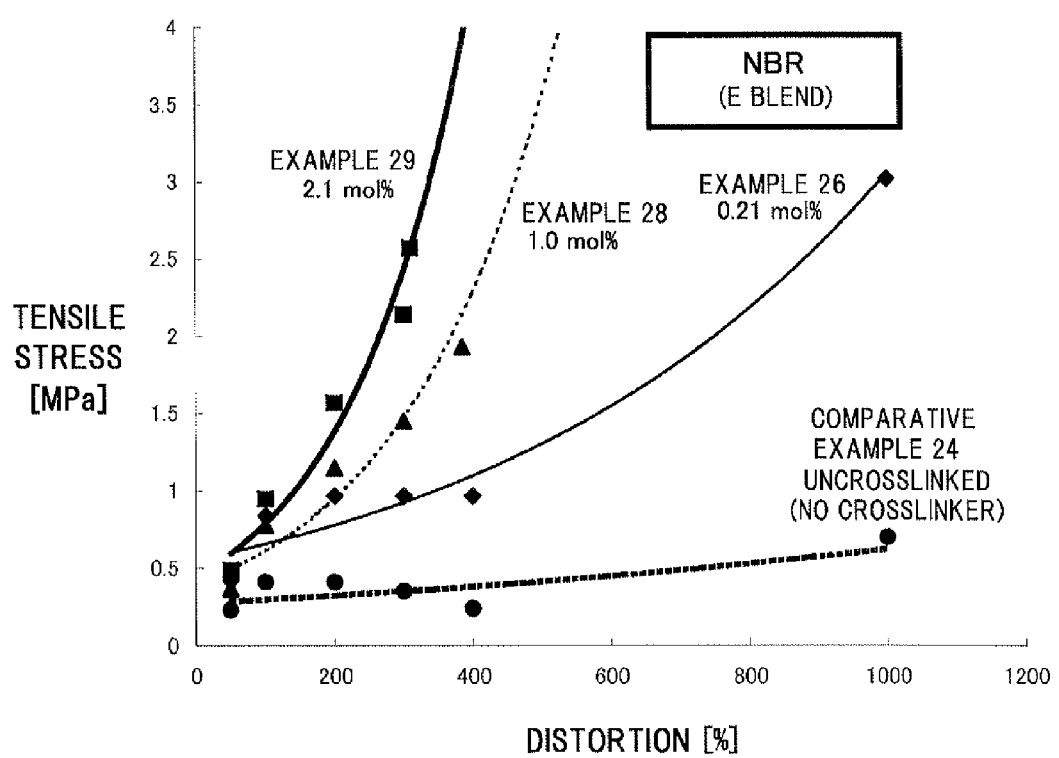
FIG. 2 is a graph showing a relationship between distortion and tensile stress in NBR in which a bifunctional nitrile oxide E is blended.

As Examples of the present invention, using the following four types of bifunctional nitrile oxides, four types of polymer materials: PAN, NBR, NR, and EPDM were crosslinked.

As Comparative Examples, PAN and a nitrile oxide were reacted by a method of reacting a base with a halogenated aldoxime as a precursor of a nitrile oxide or by a method of using a monofunctional nitrile oxide.

Production (reaction) conditions of and the presence or absence of gelation in each of Examples and Comparative Examples are shown in Table 1. Here, the reagent in the column of "reagent" in Table 1 represents a bifunctional nitrile oxide and the like used for the reaction.

TABLE 1

| | Polymer Material | Reaction Condition | | | | | |
|---|---|---|---|---|---|---|---|
| | | reagent | additive | organic solvent | reaction temperature | reaction time (h) | gelation |
| Comparative Example 1 | PAN | A (2.0 eq.) | ET$_3$N | DMF | RT | 48 | X |
| Comparative Example 2 | | B (2.0 eq.) | — | DMF | 70° C. | 48 | X |
| Example 1 | | C (0.1 eq) | — | DMF | 50° C. | 1.5 | ○ |
| Example 2 | | D (0.1 eq) | — | DMF | 70° C. | 1.5 | ○ |
| Example 3 | NBR | C (0.1 eq) | — | CHCl$_3$ | 50° C. | 1.5 | ○ |
| Example 4 | (33% CN) | D (0.1 eq) | — | CHCl$_3$ | RT | 1.5 | ○ |
| Example 5 | | E (0.1 eq) | — | — | 50° C. | 1.5 | ○ |
| Example 6 | | F (0.1 eq) | — | acetone | 50° C. | 24 | ○ |
| Example 7 | | F (0.1 eq) | — | — | 50° C. | 1.5 | ○ |
| Example 8 | NR | E (0.1 eq) | — | CHCl$_3$ | 50° C. | 1.5 | ○ |
| Example 9 | | E (0.1 eq) | — | — | 70° C. | 1.5 | ○ |
| Example 10 | EPDM | E (0.1 eq) | — | CHCl$_3$ | 50° C. | 1.5 | ○ |
| Example 11 | (10% diene) | E (0.1 eq) | — | — | 50° C. | 1.5 | ○ |
| Example 12 | Liquid EPDM | E (0.1 eq) | — | — | 80° C. | 24 | ○ |

In the present Examples and Comparative Examples, the following materials were used.

As the polymer material, PAN (polyacrylonitrile), NBR (nitrile rubber), NR (natural rubber), and EPDM (ethylene-propylene-diene copolymer rubber) were used. Among them, as NBR, an NBR having a mass ratio of acrylonitrile of 33% was used, and as EPDM, an EPDM having a mass ratio of diene of 10% was used.

As the bifunctional nitrile oxide, four types of compounds of which Structural Formulae are shown in the following <1> to <4> were used.

<1> 3,3'-[1,3-phenylenebis(carbonyl)]bis(2,6-dimethoxybenzonitrile oxide) . . . bifunctional nitrile oxide C (see Chemical Formula 1)

(Chemical Formula 1)

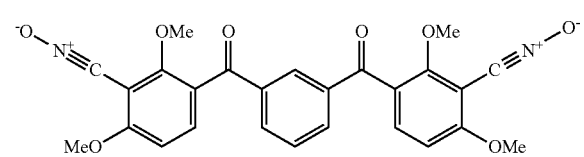

C

This 3,3'-[1,3-phenylenebis(carbonyl)]bis(2,6-dimethoxybenzonitrile oxide) was synthesized as follows.

(Chemical Formula 2)

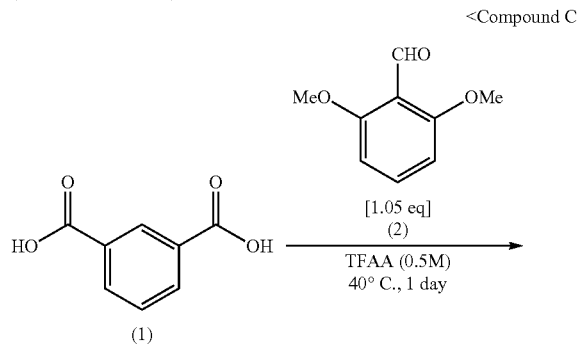

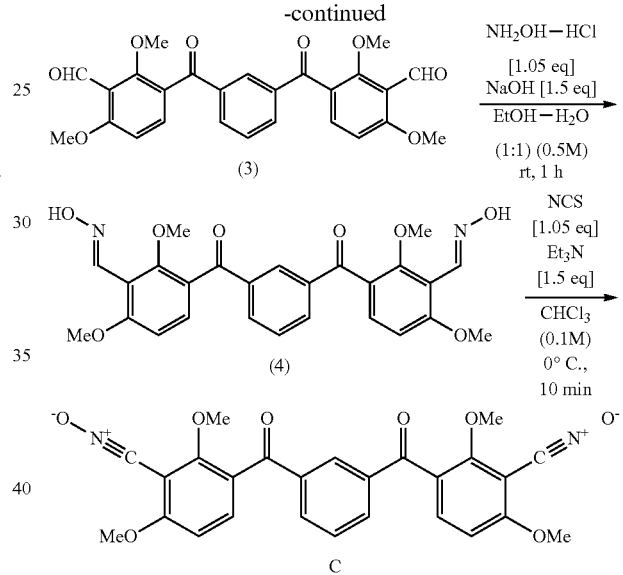

Synthesis of Bifunctional Aldehyde (3)

As shown in Chemical Formula 2, to 3.00 mL of trifluoroacetic anhydride (TFAA) in which 500 mg (3.01 mmol) of 2,6-dimethoxybenzaldehyde (2) was stirred at room temperature in an argon atmosphere, 209 mg (1.43 mmol) of isophthalic acid (1) was added, and the resultant reaction mixture was heated to 40° C., followed by effecting the reaction for 1 day. Then, the reaction system was returned to room temperature, and thereto, chloroform was added, followed by washing the reaction mixture with pure water and a 2N NaOH aq. (2N sodium hydroxide aqueous solution). Then, the solvent was concentrated under reduced pressure to obtain 560 mg (1.21 mmol, 84%) of a bifunctional aldehyde (3) as a white solid.

Synthesis of Bifunctional Oxime (4)

As shown in Chemical Formula 2, into 5.00 mL of EtOH (ethanol) in which 200 mg (0.432 mmol) of a bifunctional aldehyde (3) was suspended at 0° C. in air, a solution of 167 mg (2.41 mmol) of hydroxylamine hydrochloride and 120 mg (3.01 mmol) of NaOH in 1.00 mL of pure water was dropped. Then, the reaction was effected at room temperature for 1 hour and subsequently at 50° C. for 2 hours. Then, the reaction system was returned to room temperature, and the reaction mixture was filtered. The resultant residue was washed with pure water and chloroform and was dried to obtain 345 mg (0.71 mmol, 71%) of a bifunctional oxime (4) as a white powder.

Synthesis of Bifunctional Nitrile Oxide C

As shown in Chemical Formula 2, into 50.0 mL of chloroform in which 2.50 g (5.08 mmol) of a bifunctional oxime (4) was stirred at 0° C., 1.55 mL (10.7 mmol) of triethylamine was dropped, and thereto, 1.42 g (11.2 mmol) of N-chlorosuccinimide (NCS) was added, followed by effecting the reaction for 10 minutes. Then, the reaction solution was dropped into a two-phase system of chloroform/water, and the organic phase was washed with pure water and brine. Then, the organic phase was dried over magnesium sulfate anhydride and was filtered off, and in the resultant filtrate, the solvent was concentrated under reduced pressure to obtain a crude. Then, the crude was dissolved in a small amount of chloroform, and the resultant solution was subjected to re-precipitation in a solvent mixture of ethyl acetate/hexane=2/3 (V/V) to obtain 1.90 g (3.86 mmol, 76%) of a bifunctional nitrile oxide C as a white powder.

<2> 2,2'-[methylenebis[(2,6-dimethyl-4,1-phenylene)oxy]]bis(6-methoxybenzonitrile oxide) . . . bifunctional nitrile oxide D (see Chemical Formula 3)

(Chemical Formula 3)

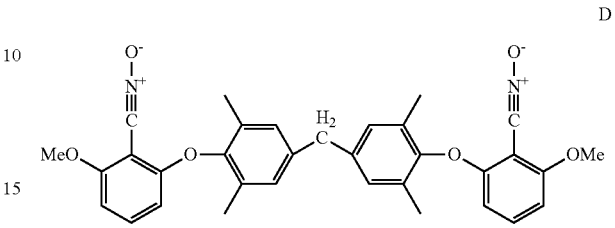

This 2,2'-[methylenebis[(2,6-dimethyl-4,1-phenylene)oxy]]bis(6-methoxybenzonitrile oxide) was synthesized as follows.

(Chemical Formula 4)

<Compound D>

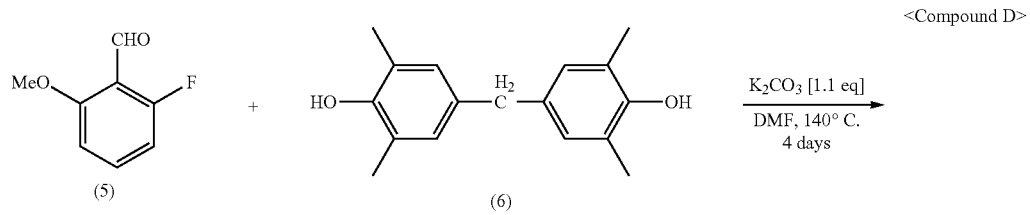

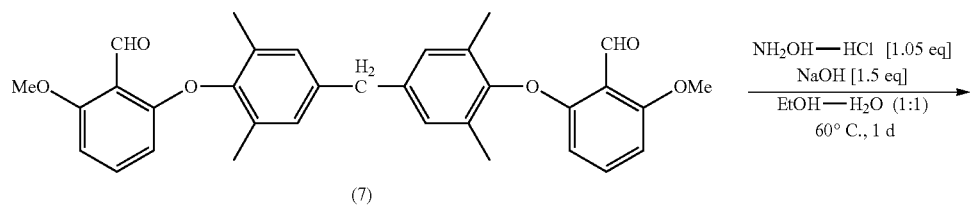

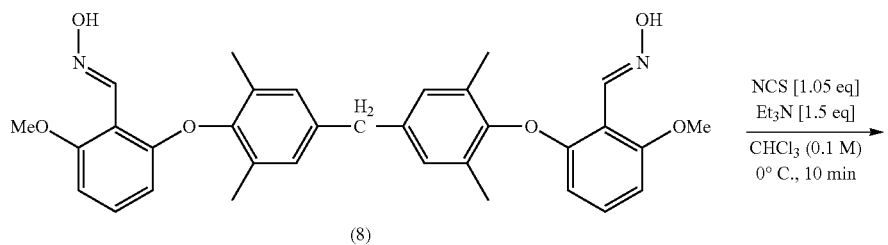

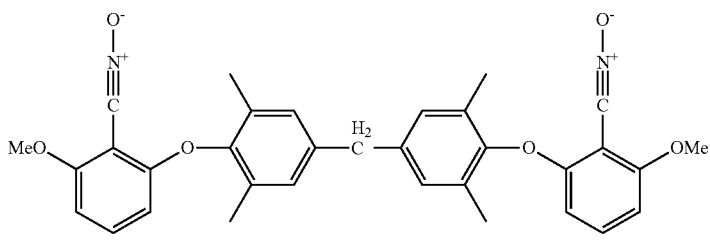

Synthesis of Bifunctional Aldehyde (7)

As shown in Chemical Formula 4, to 15 mL of DMF in which 3.78 g (14.7 mmol) of 4,4'-methylenebis(2,6-dimethylphenol) (6) and 5.00 g (32.4 mmol) of 2-fluoro-6-methoxybenzaldehyde (5) were stirred at room temperature in an argon atmosphere, 4.48 g (32.4 mmol) of potassium carbonate was added, and the resultant reaction mixture was stirred at 140° C. for 4 days. Then, the reaction system was returned to room temperature, and thereto, pure water was added, followed by extracting the reaction mixture with ethyl acetate. The organic phase was washed with pure water and brine. Then, the organic phase was dried over magnesium sulfate anhydride and was filtered off, and in the resultant filtrate, the solvent was concentrated under reduced pressure to obtain a crude. Then, the crude was purified by silica gel column chromatography (eluent: hexane:AcOEt (ethyl acetate)=2:1(v/v), Rf=0.25) and by recrystallization (eluent: hexane:AcOEt (ethyl acetate)=1:2 (v/v)) to obtain 4.91 g (9.36 mmol, 64%) of a bifunctional aldehyde (7) as a colorless crystal.

Synthesis of Bifunctional Oxime (8)

As shown in Chemical Formula 4, into 20 mL of EtOH (ethanol) in which 4.50 g (8.58 mmol) of a bifunctional aldehyde (7) was suspended at 0° C. in air, a solution of 1.25 g (18.0 mmol) of hydroxylamine hydrochloride and 1.03 g (25.7 mmol) of NaOH in 20 mL of pure water was dropped. Then, the reaction was effected at 60° C. for 1 day, and the reaction mixture was filtered. The resultant residue was washed with pure water and chloroform and was dried to obtain 4.62 g (8.33 mmol, 97%) of a bifunctional oxime (8) as a white powder.

Synthesis of Bifunctional Nitrile Oxide D

As shown in Chemical Formula 4, into 1.8 mL of chloroform in which 200 mg (0.361 mmol) of a bifunctional oxime (8) was stirred at 0° C., 110 µL (0.793 mmol) of triethylamine was dropped, and thereto, 101 mg (0.757 mmol) of N-chlorosuccinimide (NCS) was added, followed by effecting the reaction for 10 minutes. Then, the reaction solution was filtered off, and to the resultant filtrate, pure water was added, followed by extracting the resultant mixture with chloroform. The organic phase was washed with pure water and brine. Then, the organic phase was dried over magnesium sulfate anhydride and was filtered off, and in the resultant filtrate, the solvent was concentrated under reduced pressure to obtain a crude. Then, the crude was isolated by silica gel column chromatography (eluent: hexane:AcOEt (ethyl acetate)=3:2 (v/v), Rf=0.40 (eluent: hexane:AcOEt (ethyl acetate)=2:1(v/v)) to obtain 66.2 mg (0.12 mmol, 33%) of a bifunctional nitrile oxide D as a white powder.

<3> 2,2'-[isopropylidenebis[(2,6-dimethyl-4,1-phenylene)oxy]]bis(6-methoxybenzonitrile oxide) . . . bifunctional nitrile oxide E (see Chemical Formula 5)

(Chemical Formula 5)

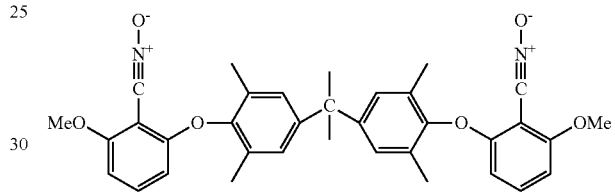

E

This 2,2'-[isopropylidenebis[(2,6-dimethyl-4,1-phenylene)oxy]]bis(6-methoxybenzonitrile oxide) was synthesized as follows.

(Chemical Formula 6)

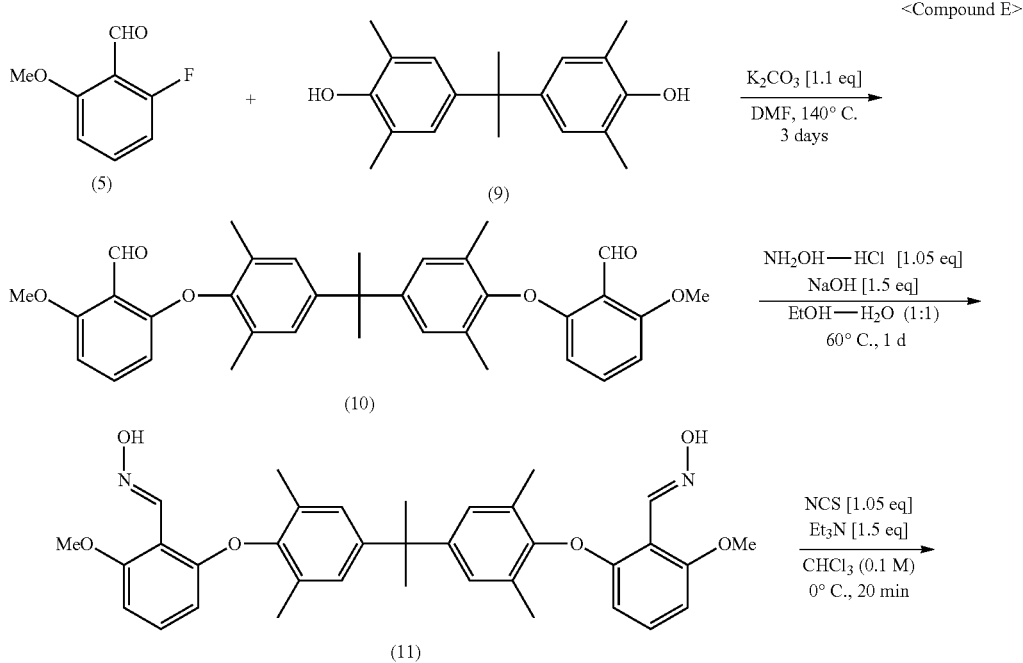

-continued

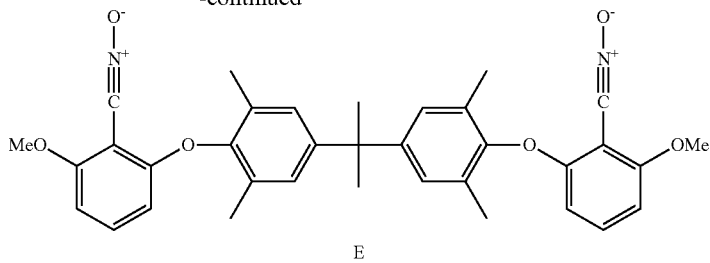

E

Synthesis of Bifunctional Aldehyde (10)

As shown in Chemical Formula 6, to 59 mL of DMF in which 16.8 g (59.0 mmol) of a bisphenol derivative (9) and 20.0 g (130 mmol) of 2-fluoro-6-methoxybenzaldehyde (5) were stirred at room temperature in an argon atmosphere, 17.9 g (130 mmol) of potassium carbonate was added, and the resultant reaction mixture was stirred at 140° C. for 3 days. Then, the system was returned to room temperature, and thereto, pure water was added, followed by extracting the reaction mixture with chloroform. The organic phase was washed with pure water and brine. Then, the organic phase was dried over magnesium sulfate anhydride and was filtered off, and in the resultant filtrate, the solvent was concentrated under reduced pressure to obtain a crude. Then, the crude was isolated by silica gel column chromatography (eluent: hexane:AcOEt (ethyl acetate)=1:1(v/v)) to obtain 297 g (91%) of a bifunctional aldehyde (10) as a white powder.

Synthesis of Bifunctional Oxime (11)

As shown in Chemical Formula 6, into 120 mL of EtOH (ethanol) in which 27.1 g (49.0 mmol) of a bifunctional aldehyde (10) was suspended at 0° C. in air, a solution of 7.50 g (108 mmol) of hydroxylamine hydrochloride and 5.88 g (147 mmol) of NaOH in 120 mL of pure water was dropped. Then, the reaction was effected at 60° C. for 1 day, and the reaction mixture was filtered. The resultant residue was washed with pure water and brine and was extracted with chloroform. Then, the organic phase was dried over magnesium sulfate anhydride and was filtered off, and in the resultant filtrate, the solvent was concentrated under reduced pressure to obtain 28.2 g (99%) of a bifunctional oxime (11) as a white powder.

Synthesis of Bifunctional Nitrile Oxide E

As shown in Chemical Formula 6, into 120 mL of chloroform in which 1.0 g (1.72 mmol) of a bifunctional oxime (11) was stirred at 0° C., 717 μL (5.15 mmol) of triethylamine was dropped, and thereto, 687 mg (5.15 mmol) of N-chlorosuccinimide (NCS) was added, followed by effecting the reaction for 20 minutes. Then, to the system, pure water was added, and the reaction mixture was extracted with chloroform, followed by washing the organic phase with pure water and brine. Then, the organic phase was dried over magnesium sulfate anhydride and was filtered off, and in the resultant filtrate, the solvent was concentrated under reduced pressure to obtain a crude. Then, the crude was isolated by silica gel column chromatography (eluent: hexane:AcOEt (ethyl acetate)=1:3 (v/v)) to obtain 975 mg (98%) of a bifunctional nitrile oxide E as a white powder.

<4> 2,2'-octamethylenebis(oxy)bis(1-naphthonitrile oxide) . . . bifunctional nitrile oxide F (see Chemical Formula 7)

(Chemical Formula 7)

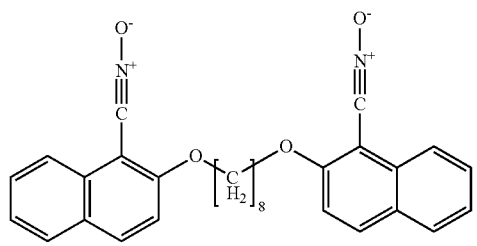

F

This 2,2'-octamethylenebis(oxy)bis(1-naphthonitrile oxide) was synthesized as follows.

(Chemical Formula 8)

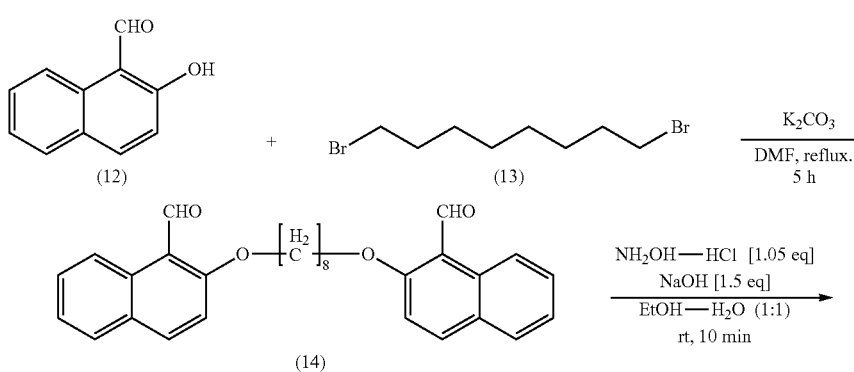

<Compound F>

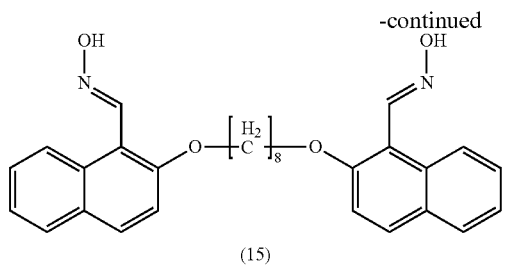

(15)

NCS [1.05 eq]
Et₃N [1.5 eq]
$\xrightarrow{\text{CHCl}_3 \text{ (0.1 M)}}$
0° C., 15 min -continued

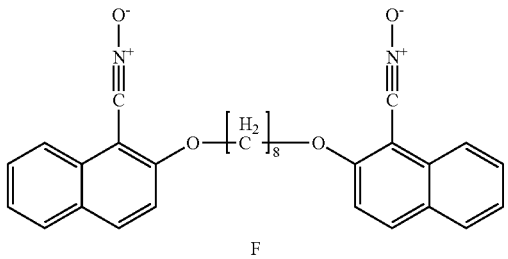

F

Synthesis of Bifunctional Aldehyde (14)

As shown in Chemical Formula 8, to 40 mL of DMF in which 6.33 g (36.8 mmol) of 2-hydroxy-1-naphthoaldehyde (12) and 3.38 mL (18.4 mmol) of 1,8-dibromooctane (13) were stirred at room temperature in air, 7.62 g (55.2 mmol) of potassium carbonate was added, and the resultant reaction mixture was refluxed for 5 hours. Then, the system was returned to room temperature, and to the reaction mixture, pure water was added, followed by filtering the reaction mixture. The resultant residue was dried to obtain a crude. Then, the crude was recrystallized in chloroform to obtain 8.16 g (18.0 mmol, 98%) of a bifunctional aldehyde (14) as a light brown crystal.

Synthesis of Bifunctional Oxime (15)

As shown in Chemical Formula 8, into 10 mL of EtOH (ethanol) in which 1.00 g (2.20 mmol) of a bifunctional aldehyde (14) was suspended at 0° C. in air, a solution of 336 mg (4.84 mmol) of hydroxylamine hydrochloride and 264 mg (6.60 mmol) of NaOH in 10 mL of pure water was dropped. Then, the reaction was effected at room temperature for 10 minutes, and to the reaction mixture, pure water was added to suspend the reaction mixture, followed by filtering the reaction mixture suspension. The resultant residue was washed with pure water and was dried to obtain a crude. Then, an acetone-soluble portion of the crude was recovered, and from the resultant solution, the solvent was distilled off under reduced pressure to obtain 493 mg (1.02 mmol, 47%) of a bifunctional oxime (15) as a white powder.

Synthesis of Bifunctional Nitrile Oxide F

As shown in Chemical Formula 8, into 40 mL of chloroform in which 100 mg (0.21 mmol) of a bifunctional oxime (15) was stirred and suspended at 0° C., 86.2 μL (0.62 mmol) of triethylamine was dropped, and thereto, 82.3 mg (0.619 mmol) of N-chlorosuccinimide (NCS) was added, followed by effecting the reaction for 15 minutes. Then, the reaction mixture was washed with pure water and was dried over magnesium sulfate anhydride. The reaction mixture was filtered off, and in the resultant filtrate, the solvent was concentrated under reduced pressure to obtain 99.2 mg (0.21 mmol, >99% of a bifunctional nitrile oxide F as a light brown crystal.

As the monofunctional nitrile oxide, a compound of Structural Formula below was used.

2,6-dimethoxybenzonitrile oxide . . . B (Chemical Formula 9)

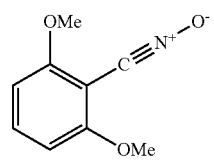

B

As the halogenated aldoxime, a compound of Structural Formula below was used.

α-benzaldoxime chloride . . . A (Chemical Formula 10)

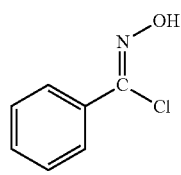

A

Next, each Example will be described.

In Example 1, PAN was dissolved in a solvent of DMF (N,N-dimethylformamide), and thereto, 0.1 equivalents of 3,3'-[1,3-phenylenebis(carbonyl)]bis(2,6-dimethoxybenzonitrile oxide) (hereinafter, may be abbreviated as C) as a bifunctional nitrile oxide was added, followed by stirring the resultant reaction mixture at a temperature of 50° C. for 1.5 hours to effect the reaction.

In Example 2, the reaction was effected under the same condition as in Example 1, except that as a bifunctional nitrile oxide, 2,2'-[methylenebis[(2,6-dimethyl-4,1-phenylene)

oxy]]bis(6-methoxybenzonitrile oxide) (hereinafter, may be abbreviated as D) was used and that the reaction temperature was changed to 70° C.

In Example 3, NBR was dissolved in a solvent of $CHCl_3$ (chloroform), and thereto, 0.1 equivalents of C as a bifunctional nitrile oxide was added, followed by stirring the resultant reaction mixture at a temperature of 50° C. for 1.5 hours to effect the reaction.

In Example 4, the reaction was effected under the same condition as in Example 3, except that as a bifunctional nitrile oxide, D was used and that the reaction temperature was changed to room temperature (RT: about 20° C.).

In Example 5, in a mortar, 0.1 equivalents of 2,2'-[isopropylidenebis[(2,6-dimethyl-4,1-phenylene)oxy]]bis(6-methoxybenzonitrile oxide) (hereinafter, may be abbreviated as E) as a bifunctional nitrile oxide was added to NBR, and the resultant reaction mixture was mixed at a temperature of 50° C. while applying pressure to the mixture for 1.5 hours to effect the reaction.

In Example 6, NBR was dissolved in a solvent of acetone, and thereto, 0.1 equivalents of 2,2'-octamethylenebis(oxy)bis(1-naphthonitrile oxide) (hereinafter, may be abbreviated as F) as a bifunctional nitrile oxide was added, followed by stirring the resultant reaction mixture at a temperature of 50° C. for 24 hours to effect the reaction. The reaction formula of this reaction is shown as follows.

(Chemical Formula 11)

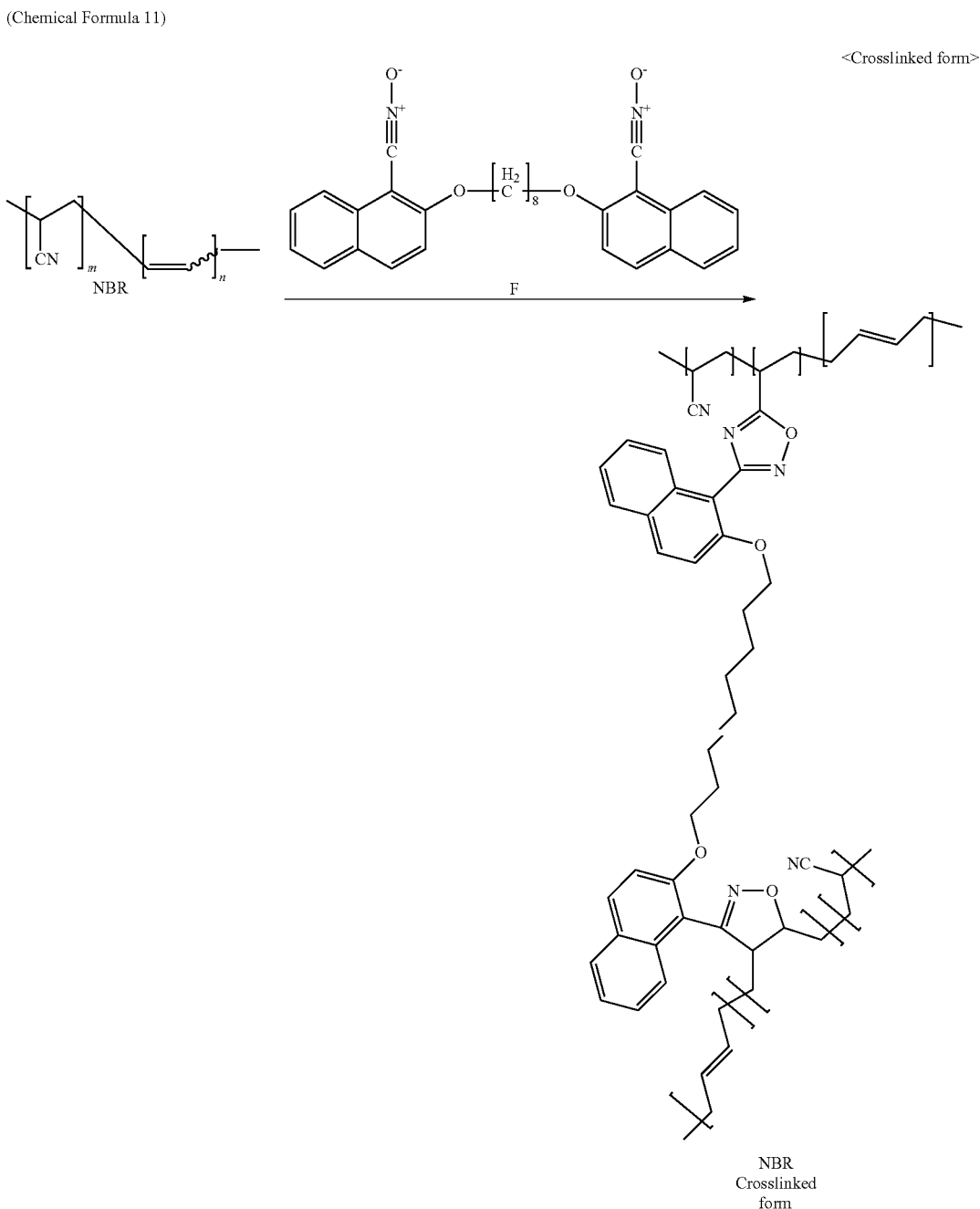

In Example 7, the reaction was effected under the same condition as in Example 5, except that as a bifunctional nitrile oxide, F was used.

In Example 8, NR was dissolved in a solvent of $CHCl_3$, and thereto, 0.1 equivalents of E was added, followed by stirring the resultant reaction mixture at a temperature of 50° C. for 1.5 hours to effect the reaction.

In Example 9, in a mortar, 0.1 equivalents of E as a bifunctional nitrile oxide was added to NR, and the resultant reaction mixture was mixed at a temperature of 70° C. while applying pressure to the mixture for 1.5 hours to effect the reaction.

In Example 10, EPDM was dissolved in a solvent of $CHCl_3$, and thereto, 0.1 equivalents of E was added, followed by stirring the resultant reaction mixture at a temperature of 50° C. for 1.5 hours to effect the reaction.

In Example 11, in a mortar, 0.1 equivalents of E as a bifunctional nitrile oxide was added to EPDM, and the resultant reaction mixture was mixed at a temperature of 50° C. while applying pressure to the mixture for 1.5 hours to effect the reaction.

In Example 12, 0.1 equivalents of E as a bifunctional nitrile oxide was added to liquid EPDM, and the resultant reaction mixture was stirred at a temperature of 80° C. for 24 hours to effect the reaction.

Next, each Comparative Example will be described.

In Comparative Example 1, PAN was dissolved in a solvent of DMF, and thereto, 2.0 equivalents of α-benzaldoxime chloride (hereinafter, may be abbreviated as A) as a precursor of a nitrile oxide was added, followed by adding thereto, $Et_3N$ (triethylamine) as an additive and stirring the resultant reaction mixture at room temperature (RT: about 20° C.) for 48 hours to effect the reaction.

In Comparative Example 2, PAN was dissolved in a solvent of DMF, and thereto, 2.0 equivalents of 2,6-dimethoxybenzonitrile oxide (hereinafter, may be abbreviated as B) as a monofunctional nitrile oxide was added, followed by stirring the resultant reaction mixture at a temperature of 70° C. for 48 hours to effect the reaction.

(1) Gelation

It was confirmed whether a crosslinked polymer material was formed or not by the above-described reaction, according to the state in which the product was dissolved in an organic solvent.

Specifically, according to whether each product after the reaction immersed in an organic solvent (DMF when the polymer material was PAN, and $CHCl_3$ when the polymer material was other than PAN) became gelatinous or dissolved without being gelatinous, the presence or absence of the formation of a crosslinked polymer material was confirmed.

A product that became gelatinous, that is, a crosslinked polymer material was formed, was evaluated as "○", and a product that became dissolved, that is, a crosslinked polymer material was not formed, was evaluated as "X".

As shown in Table 1, in all Examples, the product immersed in an organic solvent became gelatinous, so that a crosslinked polymer material produced by crosslinking a polymer material that was PAN, NBR, NR, or EPDM could be formed in a temperature range of room temperature to 80° C. Specifically, with respect to PAN in a temperature range of 50° C. to 70° C., with respect to NBR in a temperature range of room temperature (about 20° C.) to 50° C., with respect to NR in a temperature range of 50° C. to 70° C., and with respect to EPDM in a temperature range of 50° C. to 80° C., a crosslinked polymer material could be individually formed.

In Examples 5, 7, 9, 11, and 12, crosslinking of a polymer material could be performed without using an organic solvent.

(2) Stability of Nitrile Oxide

Next, the stability of 2,2'-[isopropylidenebis[(2,6-dimethyl-4,1-phenylene)oxy]]bis(6-methoxybenzonitrile oxide) that was one of the bifunctional nitrile oxides used in Examples was measured using an NMR measuring apparatus. In addition, also with respect to 2,3,5,6-tetramethylbenzene-1,4-dinitrile oxide having two nitrile oxide groups in one benzene ring, the stability thereof was measured in the same manner.

Specifically, in a state in which each sample was dissolved in DMSO-d6 and the resultant solution was heated to 80° C., the time in which the amount of each sample became half (half-life) was measured by an NMR measuring apparatus.

According to the measurement, it was found that the half-life of 2,2'-[isopropylidenebis[(2,6-dimethyl-4,1-phenylene)oxy]]bis(6-methoxybenzonitrile oxide) was about 2 hours.

On the other hand, the half-life of 2,3,5,6-tetramethylbenzene-1,4-dinitrile oxide was found to be about 1 hour.

From the measurement result of the stability, it was found that a bifunctional nitrile oxide having one nitrile oxide group in each different aromatic ring was more stable than a bifunctional nitrile oxide having two nitrile oxide groups in one benzene ring.

(3) Physical Properties Measurement

Next, there were produced film-shaped Examples in which the blending ratio of the bifunctional nitrile oxide was varied in a range of 1.0 to 10% by mass. Moreover, there were also produced film-shaped Comparative Examples in which crosslinking was not performed or for which, as a crosslinking agent, sulfur or a peroxide was used. Then, with respect to these samples, the swelling test and the tensile test were performed to measure the physical properties of the samples, and the result of the measurement is shown in Table 2. Here, the value in the parenthesis in the blending ratio column of Table 2 represents the molar fraction of a functional group of a nitrile oxide relative to a multiple bond (carbon-carbon double bond and nitrile group) of a polymer material. E-0x in the column of the network chain concentration represents a negative power of 10, and for example, 1.40E-05 represents $1.40 \times 10^{-5}$.

Figure 3:
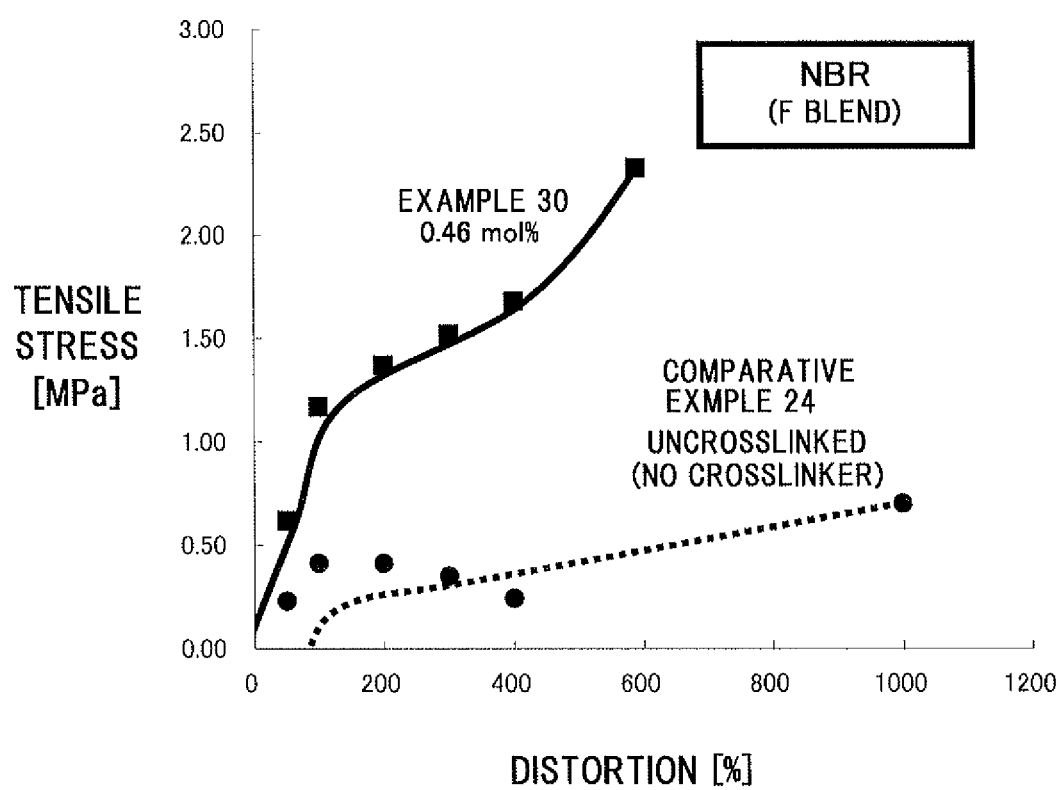
FIG. 3 is a graph showing a relationship between distortion and tensile stress in NBR in which a bifunctional nitrile oxide F is blended.

Graphs for the relationship between a distortion and a tensile stress in Examples 21 to 26, 28, and 29 and Comparative Examples 21 and 24 are shown in FIGS. 1 and 2, and a graph for the relationship between a distortion and a tensile stress in Example 30 and Comparative Example 24 is shown in FIG. 3.

TABLE 2

| | Polymer material | Crosslinker | Blending ratio | Swelling test | | Tensile test | |
| --- | --- | --- | --- | --- | --- | --- | --- |
| | | | | Swelling degree (%) | Network chain concentration ν (mol/cm³) | Tensile strength (MPa) | Elongation at break (%) |
| Comparative Example 21 | NR | — | — | — | — | 6.34 | 1100 |

TABLE 2-continued

| | Polymer material | Crosslinker | Blending ratio | Swelling test Swelling degree (%) | Network chain concentration v (mol/cm$^3$) | Tensile test Tensile strength (MPa) | Elongation at break (%) |
|---|---|---|---|---|---|---|---|
| Example 21 | | E | 1.0% by mass (0.24 mol %) | 1400 | 1.40E−05 | 6.48 | 1000 |
| Example 22 | | E | 2.0% by mass (0.48 mol %) | 890 | 3.10E−05 | 11.0 | 995 |
| Example 23 | | E | 5.0% by mass (1.2 mol %) | 610 | 6.10E−05 | 11.7 | 700 |
| Example 24 | | E | 8.5% by mass (2.0 mol %) | 500 | 9.00E−05 | 12.4 | 600 |
| Example 25 | | E | 10% by mass (2.4 mol %) | 440 | 1.10E−04 | 6.74 | 445 |
| Comparative Example 22 | | Sulfur | | 470 | 8.90E−05 | 5.30 | 645 |
| Comparative Example 23 | | Peroxide | | 290 | 2.20E−04 | 3.51 | 288 |
| Comparative Example 24 | NBR (CN: 33%) | — | | — | — | 0.70 | 1000 |
| Example 26 | | E | 1.0% by mass (0.21 mol %) | 3400 | 1.70E−05 | 3.02 | 1000 |
| Example 27 | | E | 2.0% by mass (0.41 mol %) | 1800 | 5.10E−05 | 2.17 | 718 |
| Example 28 | | E | 5.0% by mass (1.0 mol %) | 1200 | 9.90E−05 | 1.93 | 385 |
| Example 29 | | E | 10% by mass (2.1 mol %) | 1000 | 1.30E−04 | 2.57 | 310 |
| Example 30 | | F | 2.0% by mass (0.46 mol %) | 1900 | 4.70E−05 | 2.33 | 590 |

In the present Examples and Comparative Examples, the following materials were used.

As the polymer material, an NBR (nitrile rubber) in which the mass ratio of NR (natural rubber) and acrylonitrile is 33% was used.

As the bifunctional nitrile oxide that is the crosslinker in Examples, 2,2'-[isopropylidenebis[(2,6-dimethyl-4,1-phenylene)oxy]]bis(6-methoxybenzonitrile oxide) (hereinafter, may be abbreviated as E) or 2,2'-octamethylenebis(oxy)bis (1-naphthonitrile oxide) (hereinafter, may be abbreviated as F) was used.

As the crosslinker in Comparative Examples, sulfur or a peroxide was used. Here, as the peroxide, dicumyl peroxide diluted to 40% by mass was used.

Next, each Example will be described.

In Example 21, a solution in which 2.57 g of NR was dissolved in 50 mL of chloroform was charged into a fluorinated resin petri dish having a diameter of 60 mm, and thereto, a solution in which 26.0 mg of E as a bifunctional nitrile oxide was dissolved in 1 mL of chloroform was added to stir the resultant mixture. Then, a stirring rod was removed, and the inside of the petri dish was deaerated (10 Torr) with a diaphragm for 10 minutes. Subsequently, the petri dish was placed on a hot plate of 40° C. and was left standing still in an open system for 1 day. Then, the generated film was immersed in chloroform for 1 day and was dried at room temperature in atmosphere and at 50° C. in vacuum to prepare a sample in a light yellow film shape.

Example 22 was performed in the same manner as in Example 21, except that the amount of NR and the amount of E as a bifunctional nitrile oxide were changed to 2.55 g and 52.0 mg, respectively.

Example 23 was performed in the same manner as in Example 21, except that the amount of NR and the amount of E as a bifunctional nitrile oxide were changed to 2.47 g and 130 mg, respectively.

Example 24 was performed in the same manner as in Example 21, except that a solution in which 1.20 g of NR was dissolved in 18 mL of chloroform was charged into a fluorinated resin petri dish having a diameter of 42 mm and that the amount of E as a bifunctional nitrile oxide was changed to 102 mg.

Example 25 was performed in the same manner as in Example 21, except that the amount of NR and the amount of E as a bifunctional nitrile oxide were changed to 2.34 g and 260 mg, respectively.

In Example 26, a solution in which 2.57 g of NBR was dissolved in 50 mL of acetone was charged into a fluorinated resin petri dish having a diameter of 60 mm, and thereto, a solution in which 26.0 mg of E as a bifunctional nitrile oxide was dissolved in 1 mL of acetone was added to stir the resultant mixture. Then, a stirring rod was removed, and the inside of the petri dish was deaerated (10 Torr) with a diaphragm for 10 minutes. Subsequently, the petri dish was placed on a hot plate of 35° C. and was left standing still in an open system for 1 day. Then, the generated film was immersed in chloroform for 1 day and was dried at room temperature in atmosphere and at 50° C. in vacuum to prepare a sample in an opaque white film shape.

Example 27 was performed in the same manner as in Example 26, except that the amount of NBR and the amount of E as a bifunctional nitrile oxide were changed to 2.55 g and 52.0 mg, respectively.

Example 28 was performed in the same manner as in Example 26, except that the amount of NBR and the amount of E as a bifunctional nitrile oxide were changed to 2.47 g and 130 mg, respectively.

Example 29 was performed in the same manner as in Example 26, except that the amount of NBR and the amount of E as a bifunctional nitrile oxide were changed to 2.34 g and 260 mg, respectively.

In Example 30, a solution in which 2.55 g of NBR was dissolved in 40 mL of acetone was charged into a fluorinated resin petri dish having a diameter of 60 mm, and thereto, a solution in which 52.0 mg (108 µmol) of F as a bifunctional nitrile oxide was dissolved in 1 mL of acetone was added to stir the resultant mixture. Then, a stirring rod was removed, and the inside of the petri dish was deaerated (10 Torr) with a diaphragm for 10 minutes. Subsequently, the petri dish was placed on a hot plate of 35° C. and was left standing still in an open system for 1 day. Then, the generated film was immersed in acetone for 1 day and was dried at room temperature in atmosphere and at 50° C. in vacuum to prepare 2.40 g (92%) of a sample in a colorless film shape.

Next, each Comparative Example will be described.
Comparative Example 21 is an uncrosslinked NR.
Comparative Example 24 is an uncrosslinked NBR.
In Comparative Example 22, a composition in which 7 g of sulfur as a crosslinker was blended with 200 g of NR was prepared according to JIS K 6299: 2001 "Rubber—preparing method of sample for test".

In Comparative Example 23, a composition in which 17.5 g of a peroxide as a crosslinker was blended with 200 g of NR was prepared according to JIS K 6299: 2001 "Rubber—preparing method of sample for test".

(a) Swelling Test

Using a film-shaped sample prepared as described above, a test piece in a square shape having one side of 1.0 cm was prepared. This test piece was washed, well-dried, immersed in an organic solvent (for a sample composed of NR and a sample composed of NBR, toluene and dichloromethane were used, respectively), and was left standing still for 1 day to perform the test.

With respect to the test piece thus immersed in an organic solvent, the value calculated by subtracting the weight of the test piece before the test (immersion) from the weight of the test piece immediately after the test (immersion) was divided by the weight of the test piece before the test to calculate the swelling degree.

Using modified Flory-Rehner Formula:

$$v = -\frac{g}{V}\left[\frac{\ln(1-V_R) + V_R + \mu V_R^2}{g^{2/3}V_R^{1/3} - V_R/2}\right] \quad \text{(Formula 1)}$$

V: molecular volume of organic solvent (toluene or dichloromethane)
g: volume fraction of crosslinked polymer material in test piece before test
μ: interaction constant between organic solvent and sample (NR or NBR)
$V_R$: volume fraction of crosslinked polymer material in swollen test piece,
the network chain concentration v was calculated.

(b) Tensile Test

The tensile test was performed according to JIS K 6251 "vulcanized rubber and thermoplastic rubber—obtaining method of tensile properties".

From the result of the physical properties measurement, it was found that by increasing the amount of 2,2'-[isopropylidenebis[(2,6-dimethyl-4,1-phenylene)oxy]]bis(6-methoxybenzonitrile oxide) blended with NR or NBR, the values of swelling degree and of elongation at break became smaller, and on the contrary, the network chain concentration became larger. Accordingly, by 2,2'-[isopropylidenebis[(2,6-dimethyl-4,1-phenylene)oxy]]bis(6-methoxybenzonitrile oxide), NR could be crosslinked at 40° C., and NBR could be crosslinked at 35° C.

Moreover, also using 2,2'-octamethylenebis(oxy)bis(1-naphthonitrile oxide), NBR could be crosslinked at 35° C. in the same manner as in the case of 2,2'-[isopropylidenebis[(2,6-dimethyl-4,1-phenylene)oxy]]bis(6-methoxybenzonitrile oxide).

(4) Vulcanization Test

Figure 4:
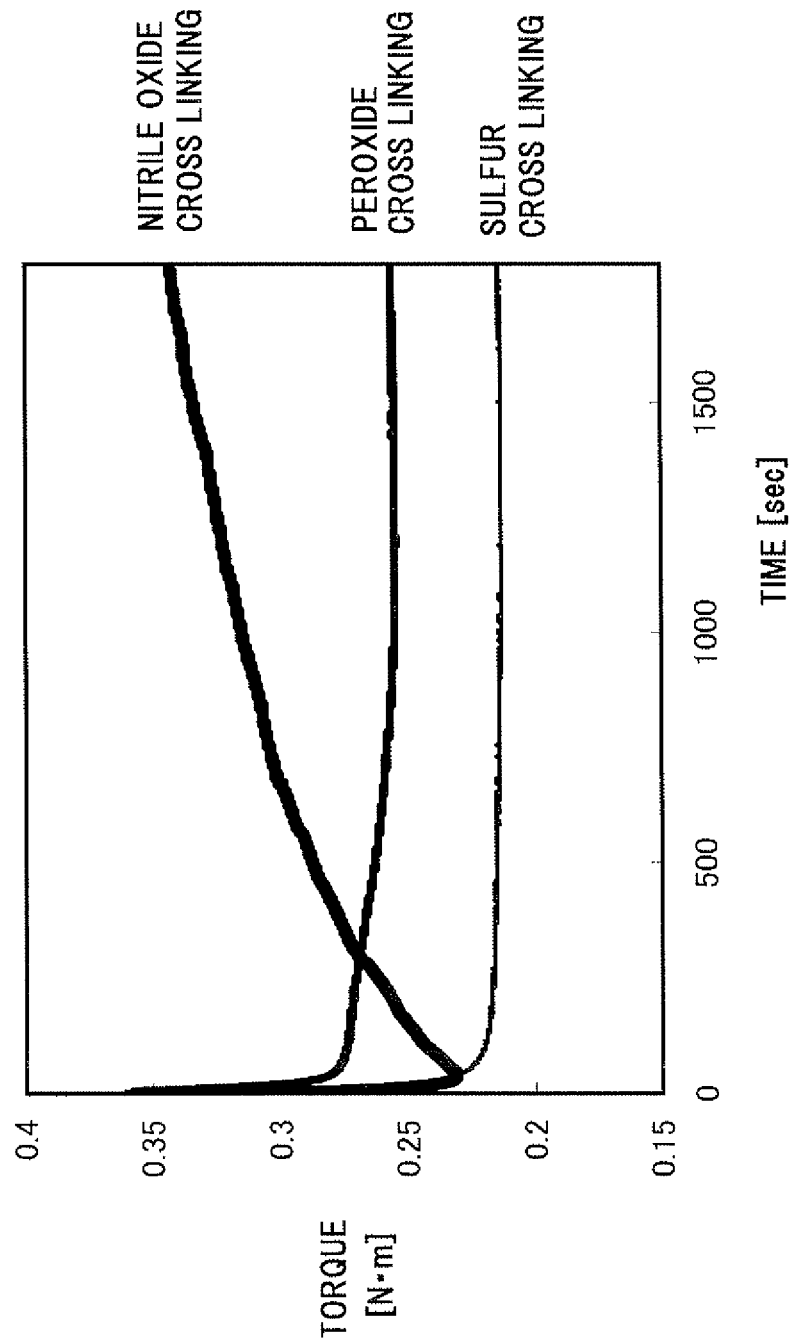
FIG. 4 is a graph showing a vulcanization curve at 100° C. of NR in which a crosslinker is blended.

Next, the vulcanization properties at 100° C. of NR with which a bifunctional nitrile oxide, sulfur, or a peroxide as a crosslinker was blended were measured according to JIS K 6300-2 "unvulcanized rubber—physical properties—second section: measuring method of vulcanization properties by an oscillating vulcanization tester", and the result (vulcanization curve) thereof is shown in FIG. 4. The formulation of each sample is shown in FIG. 3.

Figure 5:
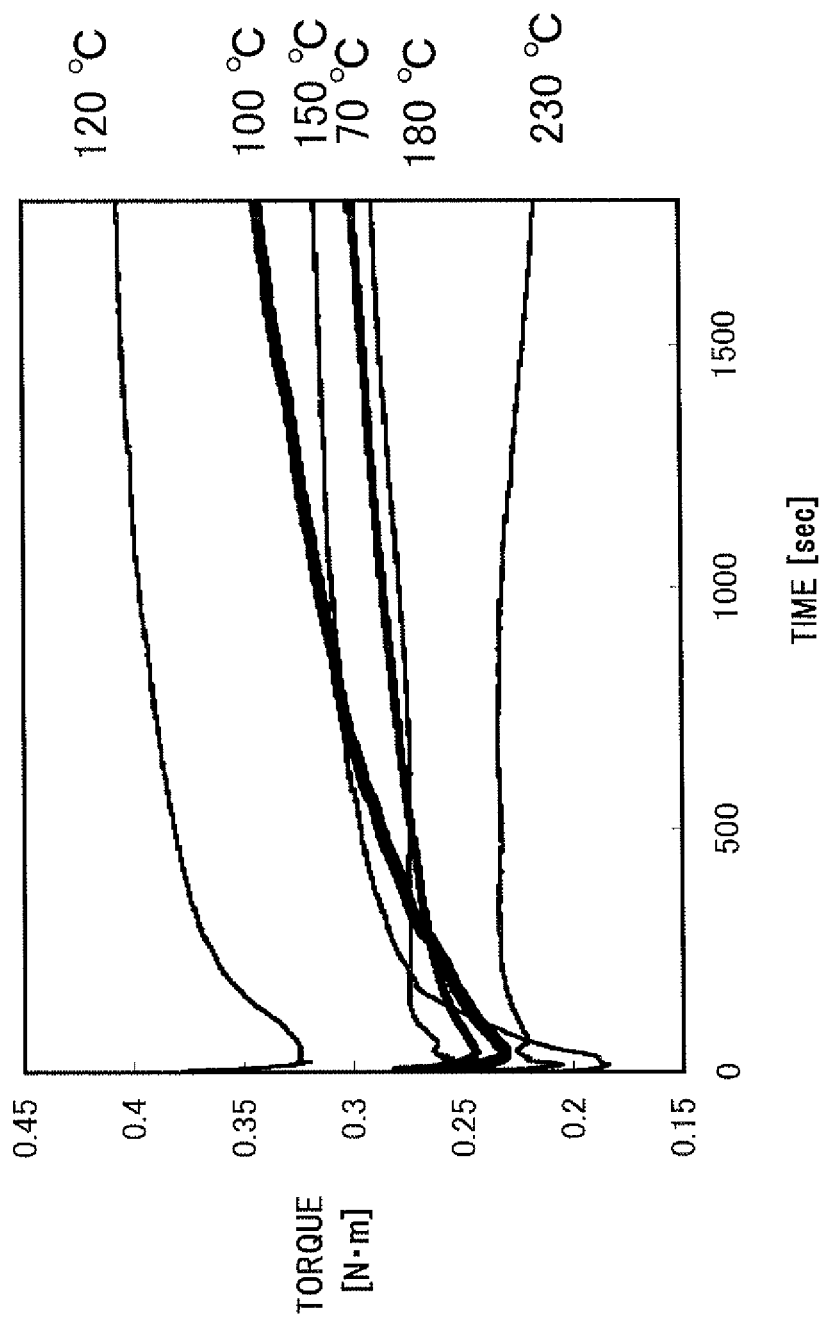
FIG. 5 is a graph showing a vulcanization curve at 70° C. to 230° C. of NR in which a crosslinker of a bifunctional nitrile oxide is blended.

With respect to a material in which a bifunctional nitrile oxide was blended, the vulcanization properties when the temperature was varied in a range of 70° C. to 230° C. were also measured, and the result (vulcanization curve) thereof is shown in FIG. 5.

TABLE 3

|  | Sulfur Crosslinking | Peroxide Crosslinking | Nitrile oxide Crosslinking |
|---|---|---|---|
| NR (natural rubber) | 200 g | 200 g | 200 g |
| Sulfur | 7.00 g |  |  |
| Peroxide |  | 17.5 g (7.00 g) |  |
| Bifunctional nitrile oxide |  |  | 7.00 g |
| Stearic acid | 1.00 g |  |  |
| ZnO | 12.0 g |  |  |
| MBT | 1.00 g |  |  |

As a bifunctional nitrile oxide that is the crosslinker in Examples, 2,2'-[isopropylidenebis[(2,6-dimethyl-4,1-phenylene)oxy]]bis(6-methoxybenzonitrile oxide) (hereinafter, may be abbreviated as E) was used.

As a peroxide, dicumyl peroxide diluted to 40% by mass was used.

As the result of the vulcanization test, as shown in FIG. 4, while a material in which sulfur or a peroxide was blended exhibited no behavior of crosslinking at all (torque was not elevated) at 100° C., in a material in which 2,2'-[isopropylidenebis[(2,6-dimethyl-4,1-phenylene)oxy]]bis(6-methoxybenzonitrile oxide) was blended, the torque was gradually elevated, so that it was indicated that the crosslinking reaction progressed.

As shown in FIG. 5, in a material in which 2,2'-[isopropylidenebis[(2,6-dimethyl-4,1-phenylene)oxy]]bis(6-methoxybenzonitrile oxide) was blended, the torque was elevated in an initial stage, so that in a temperature range of 70° C. to 230° C., the crosslinking reaction was effected. In a temperature range of 70° C. to 180° C., substantially no reversion in vulcanization (lowering of torque) was observed. At 230° C., the reversion was slightly observed. It is because a crosslinking portion is formed by a carbon-carbon covalent bond that reversion in vulcanization is thus not caused or is difficult to be caused.

From the result of the vulcanization test, a bifunctional nitrile oxide allows crosslinking of a polymer material using a kneading apparatus such as a Banbury mixer to be performed in the same manner as crosslinking using sulfur or the like.

As described above, by the crosslinker of the present Examples, polymer materials that were PAN, NBR, NR, and EPDM could be crosslinked in a temperature range of 20° C. to 230° C.

A crosslinked polymer material produced by crosslinking these polymer materials in a temperature range of 180° C. or less caused no reversion in crosslinking.

The above-described Examples should not be construed as limiting the scope of the present invention and can be embodied by being accordingly modified so long as the modification does not depart from the scope of the present invention.

The invention claimed is:
1. A crosslinker used for crosslinking a polymer material having, in the molecule thereof, a multiple bond reactable with a nitrile oxide, the crosslinker comprising:
   a bifunctional nitrile oxide having an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, wherein two such aromatic nitrile oxide derivative structures are bonded to either two oxy groups of a di-oxy structure having the two oxy groups or two carbonyl groups of a di-carbonyl structure having the two carbonyl groups.

2. The crosslinker according to claim 1, wherein the substituent is an oxy group.

3. The crosslinker according to claim 2, wherein the bifunctional nitrile oxide is
- 3,3'-[1,3-phenylenebis(carbonyl)]bis(2,6-dimethoxybenzonitrile oxide),
- 2,2'-(methylenebis[(2,6-dimethyl-4,1-phenylene)oxy]ibis(6-methoxybenzonitrile oxide),
- 2,2'-[isopropylidenebis[(2,6-dimethyl-4,1-phenylene)oxy]]bis(6-methoxybenzonitrile oxide), or
- 2,2'-octamethylenebis(oxy)bis(1-naphthonitrile oxide).

4. A production method of a crosslinked polymer material, the method comprising:
crosslinking a polymer material using a bifunctional nitrile oxide having an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, in which two such aromatic nitrile oxide derivative structures are bonded to either two oxy groups of a di-oxy structure having the two oxy groups or two carbonyl groups of a di-carbonyl structure having the two carbonyl groups: to produce the crosslinked polymer material.

5. The production method of a crosslinked polymer material according to claim 4, wherein the substituent is an oxy group.

6. The production method of a crosslinked polymer material according to claim 5, wherein the bifunctional nitrile oxide is
- 3,3'-[1,3-phenylenebis(carbonyl)]bis(2,6-dimethoxybenzonitrile oxide),
- 2,2'-[methylenebis[(2,6-dimethyl-4,1-phenylene)oxy]]bis(6-methoxybenzonitrile oxide),
- 2,2'-[isopropylidenebis[(2,6-dimethyl-4,1-phenylene)oxy]]bis(6-methoxybenzonitrile oxide), or
- 2,2'-octamethylenebis(oxy)bis(1-naphthonitrile oxide).

7. The production method of a crosslinked polymer material according to claim 4, wherein the polymer material is PAN, NBR, NR, or EPDM.

8. The production method of a crosslinked polymer material according to claim 4, wherein the crosslinking of the polymer material with the bifunctional nitrile oxide is performed without using an organic solvent.

9. The production method of a crosslinked polymer material according to claim 8, wherein the crosslinking is performed in a kneading apparatus.

10. The production method of a crosslinked polymer material according to claim 4, wherein the crosslinking of the polymer material with the bifunctional nitrile oxide is performed is an organic solvent.

11. A crosslinked polymer material produced by crosslinking a polymer material with a bifunctional nitrile oxide having an aromatic nitrile oxide derivative structure in which one hydrogen atom of an aromatic ring is substituted with a nitrile oxide group and all hydrogen atoms at an ortho-position of the nitrile oxide group are substituted with a substituent other than a nitrile oxide group, in which two such aromatic nitrile oxide derivative structures are bonded to either two oxy groups of a di-oxy structure having the two oxy groups or two carbonyl groups of a di-carbonyl structure having the two carbonyl groups.

12. The crosslinked polymer material according to claim 11, wherein the substituent is an oxy group.

13. The crosslinked polymer material according to claim 12, wherein the bifunctional nitrile oxide is
- 3,3'-[1,3-phenylenebis(carbonyl)]bis(2,6-dimethoxybenzonitrile oxide),
- 2,2'-[methylenebis[(2,6-dimethyl-4,1-phenylene)oxy]]bis(6-methoxybenzonitrile oxide),
- 2,2'-[isopropylidenebis[(2,6-dimethyl-4,1-phenylene)oxy]]bis(6-methoxybenzonitrile oxide), or
- 2,2'-octamethylenebis(oxy)bis(1-naphthonitrile oxide).

14. The crosslinked polymer material according to claim 11, wherein the polymer material is PAN, NBR, NR, or EPDM.

* * * * *